United States Patent

Lu et al.

Patent Number: 5,804,727
Date of Patent: *Sep. 8, 1998

[54] MEASUREMENT OF PHYSICAL CHARACTERISTICS OF MATERIALS BY ULTRASONIC METHODS

[75] Inventors: Wei-yang Lu, Pleasanton; Shermann Min, Livermore, both of Calif.

[73] Assignee: Sandia Corporation, Livermore, Calif.

[*] Notice: This patent issued on a continued prosecution application filed under 37 CFR 1.53(d), and is subject to the twenty year patent term provisions of 35 U.S.C. 154(a)(2).

[21] Appl. No.: 522,682

[22] Filed: Sep. 1, 1995

[51] Int. Cl.⁶ ..................................... G01H 5/00
[52] U.S. Cl. ................. 73/597; 73/643; 73/602; 73/159
[58] Field of Search .............. 73/597, 643, 600, 73/159, 602

[56] References Cited

U.S. PATENT DOCUMENTS

| | | | |
|---|---|---|---|
| 4,432,234 | 2/1984 | Jones | 73/597 |
| 4,622,853 | 11/1986 | Leugers | 73/597 |
| 4,674,332 | 6/1987 | Pace et al. | 73/597 |
| 4,838,085 | 6/1989 | Pellerin et al. | 73/597 |
| 4,899,589 | 2/1990 | Thompson et al. | 73/597 |
| 5,025,665 | 6/1991 | Keyes, IV et al. | 73/597 |
| 5,031,457 | 7/1991 | Kline | 73/597 |
| 5,033,304 | 7/1991 | Rosen | 73/597 |
| 5,035,143 | 7/1991 | Latimer et al. | 73/598 |
| 5,048,340 | 9/1991 | Thompson et al. | 73/597 |
| 5,103,676 | 4/1992 | Garcia et al. | 73/597 |
| 5,251,486 | 10/1993 | Thompson et al. | 73/597 |
| 5,286,313 | 2/1994 | Schultz et al. | 73/597 |

OTHER PUBLICATIONS

Man, C. and W. Lu "Measurement of Stress Using Ultrasonic Techniques Based on a New Acoustoelastic Theory" Proceedings of the Sixth International Conference, Beijing, People's Republic of China, vol. 2, Permagon Press Sep. 11–15, 1988 pp. 979–988.

*Primary Examiner*—Hezron E. Williams
*Assistant Examiner*—Richard A. Moller
*Attorney, Agent, or Firm*—Timothy Evans; Kurt Olsen

[57] ABSTRACT

A method is described for determining and evaluating physical characteristics of a material. In particular, the present invention provides for determining and evaluating the anisotropic characteristics of materials, especially those resulting from such manufacturing processes as rolling, forming, extruding, drawing, forging, etc. In operation, a complex ultrasonic wave is created in the material of interest by any method. The wave form may be any combination of wave types and modes and is not limited to fundamental plate modes. The velocity of propagation of selected components which make up the complex ultrasonic wave are measured and evaluated to determine the physical characteristics of the material including, texture, strain/stress, grain size, crystal structure, etc.

8 Claims, 6 Drawing Sheets

MEASUREMENT OF PHYSICAL CHARACTERISTICS OF MATERIALS BY ULTRASONIC METHODS

STATEMENT OF GOVERNMENT INTEREST

This invention was made with Government support under contract no. DE-AC04-94AL8500 awarded by the U. S. Department of Energy to Sandia Corporation. The Government has certain rights in the invention.

BACKGROUND OF THE INVENTION

This invention relates generally to a method for employing ultrasonic waveforms to evaluate and determine physical characteristics of a material.

Metal forming operations such as deep drawing, stretching, extruding and bending are all significantly influenced by the degree of crystallographic anisotropy (texture) and the resulting anisotropy in physical properties of the material. The ability to quickly and accurately determine and evaluate texture in metal plates or sheets during the manufacturing process could be efficiently employed to control the manufacture of a product having desired texture and physical characteristics or to correct for texture deficiencies as they occur. Knowledge of texture is important in predicting the ability of the metal stock to be formed into parts of complex shape. For example, a Goss component of texture is necessary in the manufacturing of quality steel transformers but undesirable in plate forming and canning applications. In addition to a metal sheet's formability and degree of earing, information about individual physical properties may also be useful in the manufacturing process.

Previously, texture analysis required periodic sampling of the continuously produced sheet or plate material. In one process, texture was then subsequently determined by x-ray or neutron diffraction analysis of samples extracted from the material. Not only does this process require a time consuming destructive sampling of the rolling mill material but it cannot be used to correct or change production processes during the rolling operation. If for some reason, the texture of the sheet product is inappropriate for its intended end use, the whole run of sheet metal must be scrapped or another use must be found. Furthermore, x-ray analysis can only characterize near surface layers of the material. On-line x-ray analysis, while giving more timely data, is still not appropriate for feedback control since data is only reported every 10 sec. This technique also presents significant personnel hazards. Neutron diffraction can provide information about the entire thickness of the material, however, samples must be taken to a neutron source to perform the analysis. Therefore, a real need exists for a non-hazardous process which permits texture analysis of sheet or plate material to be done rapidly during the processing operation itself in order to initiate manufacturing changes which would alter texture in the desired way.

Ultrasonic techniques, which measure elastic anisotropy, have also been used to measure texture and plastic anisotropy of sheet materials. Two ultrasonic techniques are favored to measure material anisotropy, the electromagnetic acoustic transducer (EMAT) method and the laser ultrasonic (LU) method. EMAT systems are usually based on the excitation of the Lamb or SH (horizontally polarized shear) waves and are typically designed to generate narrow band waves with known wave types. LU, on the other hand, is characterized by the simultaneous generation of multiple wave types and modes, the specifics of which are dependent upon the properties (duration, temporal and spatial shape, power) of the generation laser pulse(s) and the boundary conditions of the specimen. Although LU clearly distinguishes plates of different anisotropy, the results are difficult to interpret analytically due to the complicated nature of the waveform generated by a laser source.

By way of example, a method of ultrasonic measurement of textures is described by Thompson in U.S. Pat. Nos. 5,251,486; 5,048,340 and 4,899,589. This method employs electromagnetic acoustic measurements (EMAT) to determine texture in metal sheets and plates. Acoustic plate modes are generated by the interaction of a pulsed magnetic field with the surface of the metal material being analyzed. These modes are detected after traveling through the material by interaction of the moving conducting surface with a constant magnetic field. The texture characteristics are derived by measuring the time it takes for the ultrasound energy to be received by a receiving means and calculating the velocity of the ultrasound energy from the timed measurements. Texture characteristics can then be extracted from the velocity measurements.

The use of electromagnetic acoustic measurement for material characterization has the advantage that it can be done during the plate or sheet forming operation and further, it is nondestructive. However, this method suffers from the disadvantage that it is limited insofar as the plate modes that it can distinguish (plate modes is terminology from the field of physical acoustics and refers to particular sets of elastic waves in thin materials). The plate modes that can be distinguished by this method are limited to Lamb waves and shear horizontal plate mode $S_n$, $A_n$, and $SH_n$. Furthermore, the EMAT method of measuring texture requires that the transducer either abut or be closely adjacent ($\approx$1/1000th if an inch) to the surface of the metal which can be a significant disadvantage in a high speed rolling mill. This method also suffers from the limitation that travel distances must be on the order of several inches because of the physical size of the EMAT transducers. Consequently, the measurements represent an averaged value over a very large area which can be misleading or incorrect, particularly for stress measurements. Because a conducting surface is necessary, the EMAT method is limited primarily to metals.

In addition to texture, the evaluation of the state and extent of stress/strain are important parameters in engineering analysis. Strain (or deformation) can be measured accurately by many methods such as strain gages, Moirè fringes, etc. In engineering practice stress is usually calculated from the measured strain (or strain history) and the stress-strain relation of the material. The quantity obtained is actually the stress increment from a reference (or initial) state; it equals the absolute stress state only when the initial state of the body is stress-free. Although residual stresses can be obtained from the deformation due to mechanical stress relaxation (e.g. hole drilling or sectioning), they should ideally be evaluated nondestructively in the actual member under operating conditions. There is a critical need to evaluate stress independently from strain measurements.

It has been shown that the acoustoelastic effect may be useful for the nondestructive evaluation of stresses. The acoustoelastic effect refers to the fact that elastic wave velocities vary with stress, which can be conceptually described by the relation: $v=v_o+k\sigma$, where v is the wave velocity, $\sigma$ is the stress and k is the acoustoelastic constant. Accurate measurements of the stress-induced velocity changes yield information which can lead to the determination of stresses in the body. The difficulty, however, is the smallness of this velocity effect (e.g. the relative change of wave speed for aluminum is about $10^{-5}MPa^{-1}$), which leads to challenging experimental and theoretical problems. The large size of conventional ultrasonic transducers, for example, provides poor spatial resolution of the stress field. Other competing factors (e.g. the weak anisotropy of the material) which are usually ignored in the engineering application of elasticity can no longer be neglected in acoustoelasticity. Furthermore, a precision of 1 part in $10^5$ or higher is required for the measurement of wave speeds.

There is need for a new method of on-line determination and evaluation of the physical properties of materials which is non-hazardous to personnel, non-destructive, capable of high spatial resolution and with sufficient speed that the resulting information can be used to provide feedback in real time to a manufacturing process. There is a further need for the measurement of strain/stress which allows the independent evaluation of stress from strain and can do so over path lengths that are on the order of a few millimeters. Finally, it is desired that the method should be useful for both metallic and non-metallic materials.

SUMMARY OF THE INVENTION

The instant invention is a method for determining and evaluating the physical characteristics of materials from measurements of ultrasonic wave velocities. Advances by the inventors in theory and experimental techniques have made it possible to analytically examine and experimentally extract from wideband longitudinal, plate, shear and Rayleigh waves, texture-induced anisotropy and stress-induced anisotropy. The method of the instant invention also provides the ability to extract useful physical property information from wideband acoustic signals which can be applied to non-metallic materials such as polymers and glasses as well as metal materials. This method has also proved useful for determining density gradients and porosity in compacted powders.

In operation, an ultrasonic wave is created in the material of interest by any method. The wave form may be any combination of wave types and modes and is not limited to fundamental plate modes. The velocity of propagation of selected components which make up the complex ultrasonic wave are measured and evaluated to determine the physical characteristics of the material including, texture, strain/stress, grain size, crystal structure, etc.

The instant invention therefore, provides for an accurate high resolution method for determination and evaluation of physical characteristics without having to utilize destructive x-ray or neutron diffraction methods. The present invention provides for a resolution of about a millimeter, thereby improving the spatial resolution of stress measurements by at least an order of magnitude over present methods. It further provides a method that will give instantaneous feedback and thus can be used in continuous operation in a sheet forming process, thereby providing a means for changing or adjusting the process to correct texture characteristics.

DETAILED DESCRIPTION OF THE INVENTION

The essential concept of the present invention is a method of extracting from a wideband ultrasonic signal the physical characteristics of a material and to do so instantaneously.

Figure 1:
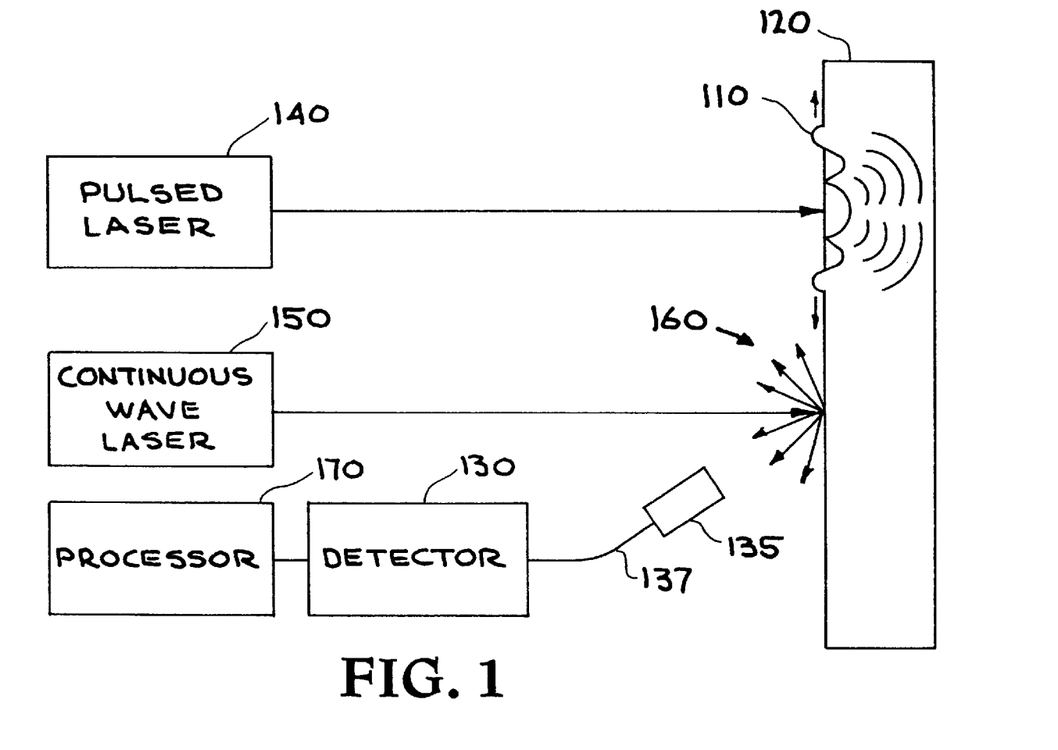
FIG. 1 is an embodiment of the operation of the instant invention.

Referring now to FIG. 1 where one embodiment of the present invention is illustrated. A wave form 110 is generated in the sample 120, preferably by means of a pulsed laser 140 such as a Nd:YAG laser producing light at any number of wavelengths (e.g., 1064, 532, 266 nm), since it is desired to employ different wavelengths for different measurements. Unlike EMAT ultrasonic methods of generating ultrasonic energy in a sample, the laser source 140 generates ultrasonic energy in the sample 120 by causing an almost instantaneous local increase in temperature. Thus this method of generating ultrasonic-pulses has application for non-metallic as well as metallic materials. Simultaneously, a timer, not shown, is started. The wave form, which may be any combination of wave types and modes and is not limited to fundamental plate modes, propagating along the surface of the sample causes light from an illumination source, preferably a continuous wave laser 150, to be scattered 160. The scattered light 160 is collected and sent to a detector 130, preferably by a collection lens 135 and a fiber optic cable 137. Those skilled in the art will recognize that any of a number of techniques useful for detection of surface or particle motion due to the passing of an ultrasonic wave may be used, e.g., Doppler velocimeter, phase sensitive detectors, although a Fabry-Perot interferometer is preferred as a means of detection due to its ability to handle optically rough surfaces (sample preparation is not necessary). Since texture measurements are dependent upon the determination of wave velocity changes, the detection system is not limited to out-of-plane disturbances caused by the passage of an ultrasonic wave; in-plane particle motion detectors are equally useful. Furthermore, if two independent detectors are used the need for a highly stable timing mechanism to trigger data acquisition is not required.

Figure 2:
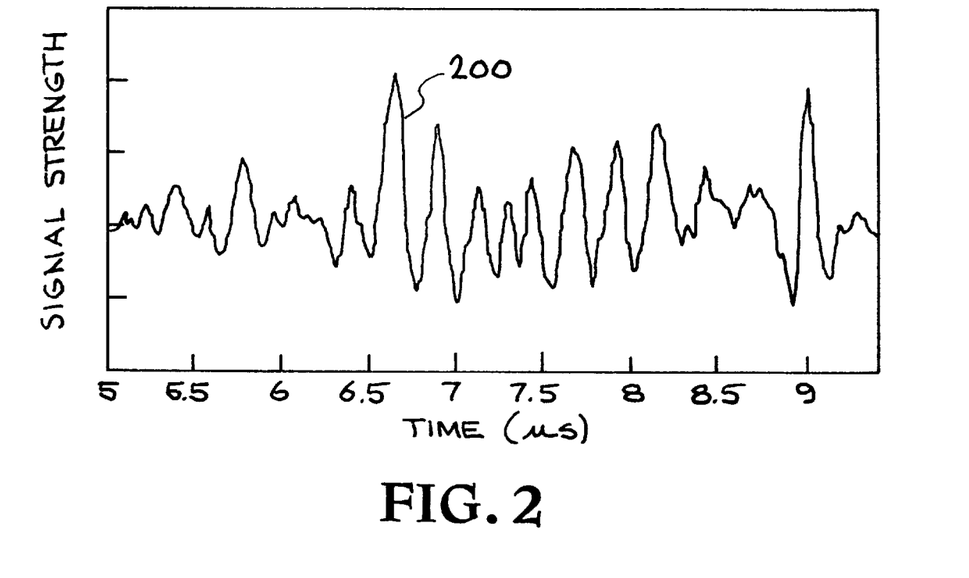
FIG. 2 shows the response of a sample to a generation source.

In FIG. 2, the signal 200 represents the response of sample 120 to the ultrasonic energy propagating therein. Unlike the more typical applications of lasers to generate ultrasonic waves in a sample, where only simple modes are excited, signal 200 clearly depicts a very complex signal wherein it will later be shown comprises components of differing modes and types of acoustic energy some of which overlap, at least temporally. This embodiment of the invention also includes a processor 170 for processing, in near real-time, signals 200 thereby providing physical characteristics of the sample.

A plurality of signals can be collected for a plurality of orientations and locations within the sample 120. The collection of a plurality of signals can typically be accomplished by rotating or translating the position of the detector 130 relative to the sample 120. For texture measurements, the orientation of such signal is typically indexed to the rolling or forming direction in which the sample was processed. In a plate or sheet of material, the rolling or forming direction is parallel to the longitudinal axis of the sheet or plate. Alternatively, multiple sources and/or detectors can be used. Misalignment of the laser beams can occur if the local normal is not perpendicular to the orientation of the sheet and can result in erroneous results, in some cases equal in magnitude to the anisotropy in the sheet. In this case, the measured propagation distance does not remain constant as assumed but varies as a function of the local surface normal. Numerical correction of the data are possible in this case. Those skilled in the art will appreciate that several other methods of correction are available, e.g., using geometrical relations to correct for this misalignment, assuming the surface normal is known, or taking advantage of known symmetries in the measurement.

A typical interferometric signal 200 is depicted in FIG. 2 for a particular orientation for an aluminum plate ⅟₃₂" thick. In order to effect a decrease in random noise and hence a clearer image of events in the signal representative of different components of the complex ultrasonic energy signal averaging of multiple activations is used. Processor 170 can be used to process signal 200 and provide measures of selected physical characteristics of the sample including texture, degree of anisotropy, tensile strength, grain size and orientation, ductility and stress state. In particular, time-of-flight (TOF) information is first extracted from signal 200 in processor 170 by extracting a waveform signal within a specified time window. The time window represents an expected time of arrival, within signal 200, for a given mode or type of ultrasonic energy thus not only reducing the time required to process signal 200 but also only extracting that data which is representative of a given process within the sample.

Figure 3A:
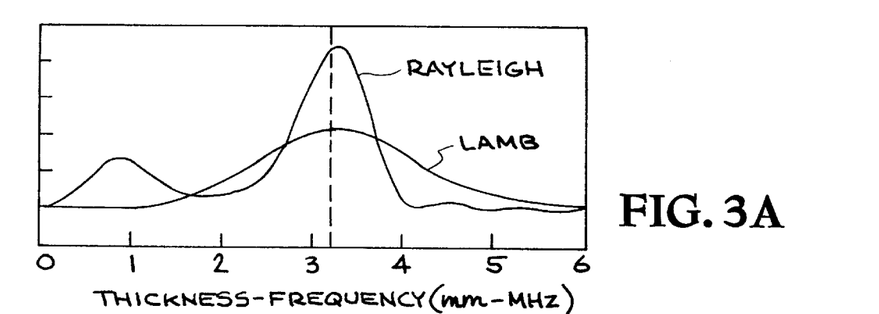
FIG. 3 shows a typical dispersion curve for aluminum.
Figure 3B:
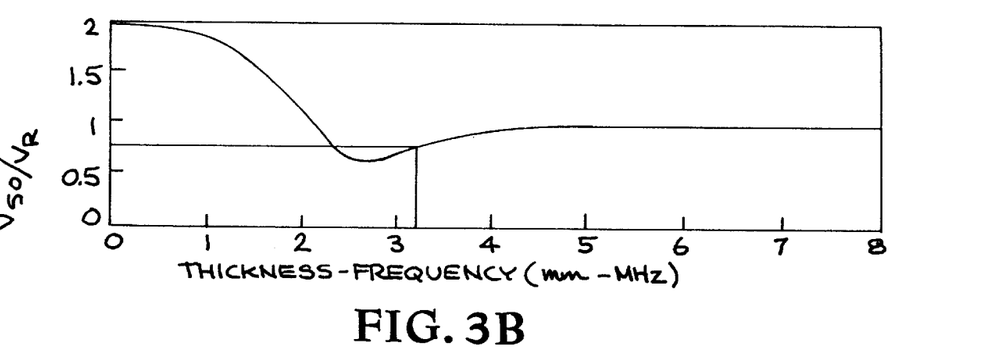
Figure 3C:
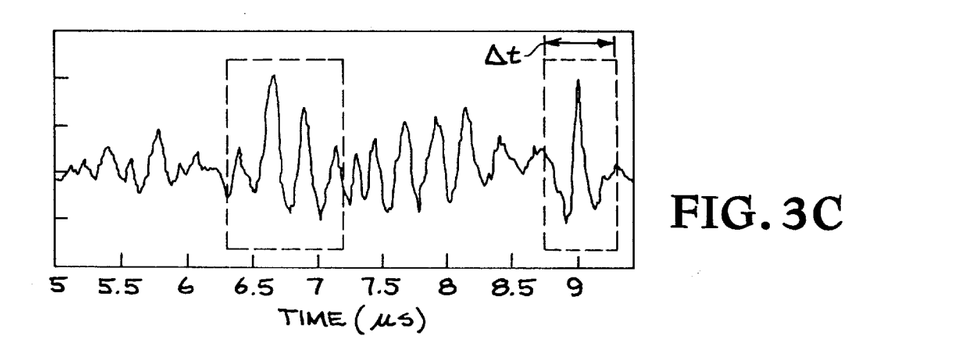

By use of dispersion curves relevant to the material composition of the sample of interest and boundary conditions for the sample (width, thickness, length, known velocity of propagation for various modes and types of ultrasonic wave propagation) time windows for different modes and types of ultrasonic waves can be determined. A digital gate is used to process a portion of the signal where a particular wave is expected to arrive, given the velocity (known) of the wave and the separation distance between the excitation and detection lasers. FIG. 3, depicts the process whereby a slowness curve is constructed using the digital gate to extract the appropriate time window. FIG. 3a shows the response of the Rayleigh and Lamb modes as a function of the product of sample thickness and frequency. It can be seen that the maxima in these two curves occurs at about 3.2 mm-MHz. This value is transferred to the curve representing the $S_o$ dispersion velocity normalized by the Rayleigh wave velocity, 3b. The value of 3.2 mm-MHz corresponds to a Lamb wave that is 0.75 that of the Rayleigh wave. Since the Rayleigh wave arrival time is 6.8 $\mu$s, the dispersion relation states that the Lamb wave should arrive at 9.0 $\mu$s. Consequently, a time window ($\Delta t$) from which power data is taken to construct the $S_o$ slowness curve is centered around 9.0 $\mu$s, FIG. 3c.

The foregoing represents a method to extract velocity information about specific wave types and modes from a complicated signal, such as signal 200. Those skilled in the art will recognize that these velocities can be used to determine physical properties such as, but not limited to, density, temperature, viscosity, texture, stress, strain, tensile strength, elastic constants, grain size and orientation, and ductility. As a specific example of the use of the method of the instant invention, velocity information obtained by the method of the instant invention was used to measure texture as set forth hereinbelow.

The TOF data are normalized by the generation source 140 to detector 130 distance to obtain a slowness or inverse velocity curve. Unlike other known ultrasonic methods, the present invention provides for extremely high resolution information since the source-detector distance can be very small, i.e., ≈1 mm. The slowness data can then be plotted as a function of the orientation from which they were collected and subsequently fitted to a curve by means of a routine developed by Man and Lu and set forth in C. S. Man and W. Y. Lu, *Pressure Vessel Technology*, (Proceedings of the Sixth International Conference), Beijing, PRC, 979–988, Sept., 1988. The equation for this curve is given by $$\rho v^2(\theta) = \alpha_1 + \alpha_2 \sin^2 \theta + \alpha_3 \sin^2 \theta \cos^2 \theta + \alpha_4 \sin^2 \theta + \alpha_5 \sin 2\theta \cos 2\theta, \quad (1)$$

where, $\rho$=density of the sample;
$v$=velocity of a mode or type of ultrasonic energy;
$\theta$=angle of orientation; and
$\Gamma_i$=coefficients of fit.

Figure 4A:
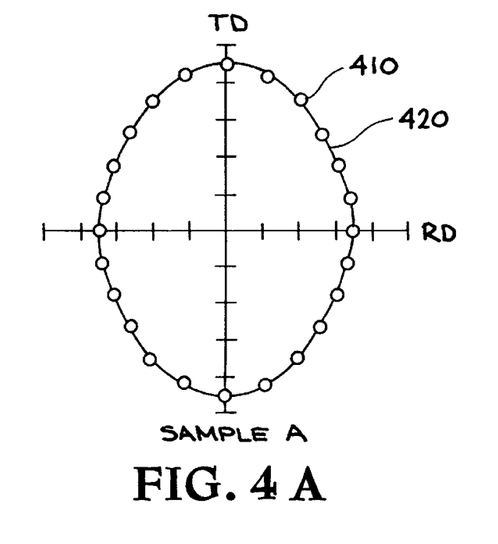
FIG. 4 shows slowness curves for two samples of aluminum at ≈6.8 $\mu$s. The open symbols are experimental data and the curve joining the symbols was derived from equation (1) (RD is the rolling direction and TD is the transverse direction).
Figure 4B:
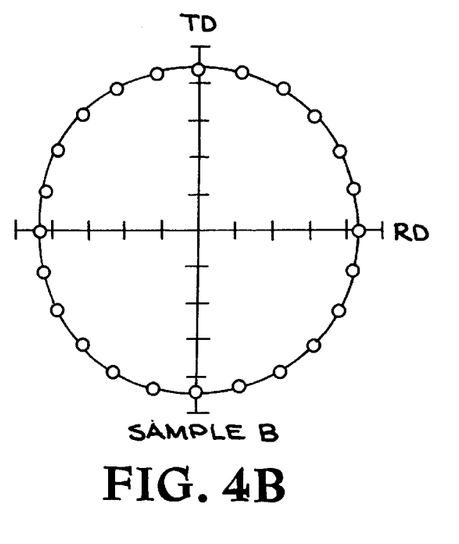
Figure 6A:
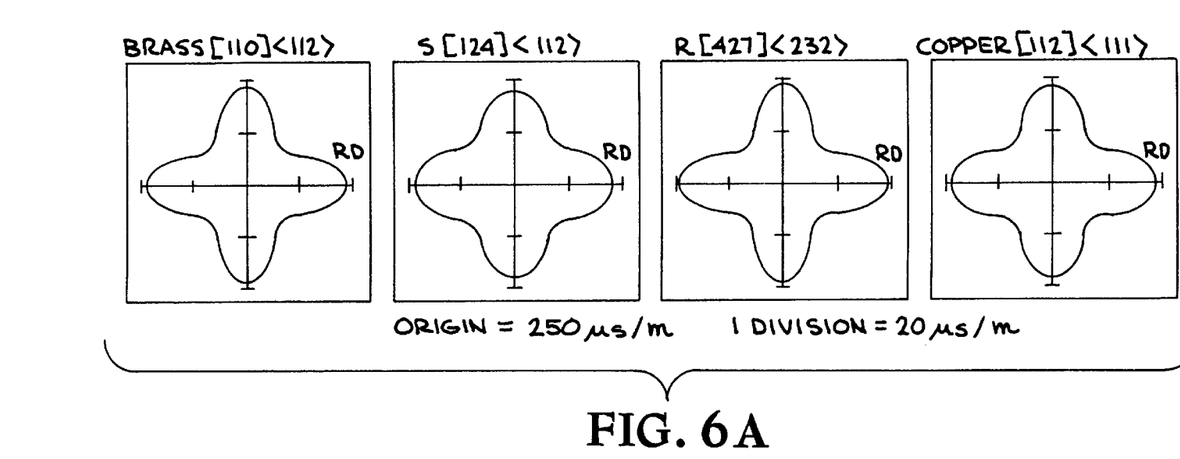
FIGS. 6–8 show calculated $SH_o$ (FIG. 6), $S_o$ (FIG. 7) and Rayleigh (FIG. 8) slowness curves for several aluminum textures:
  a) deformation textures
  b) recrystallization textures
Figure 6B:
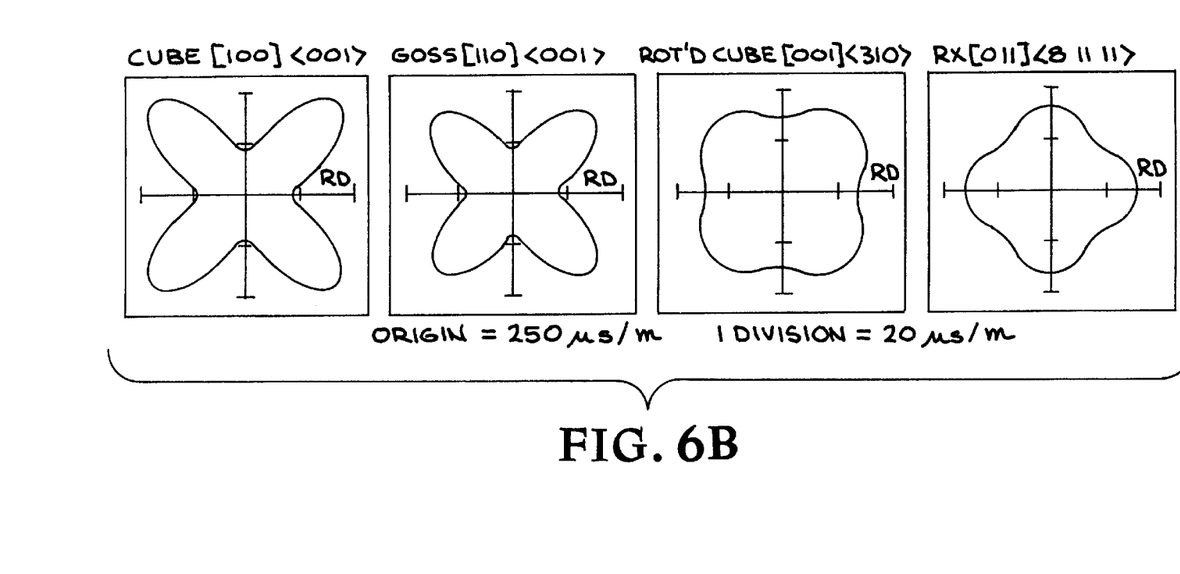
Figure 7A:
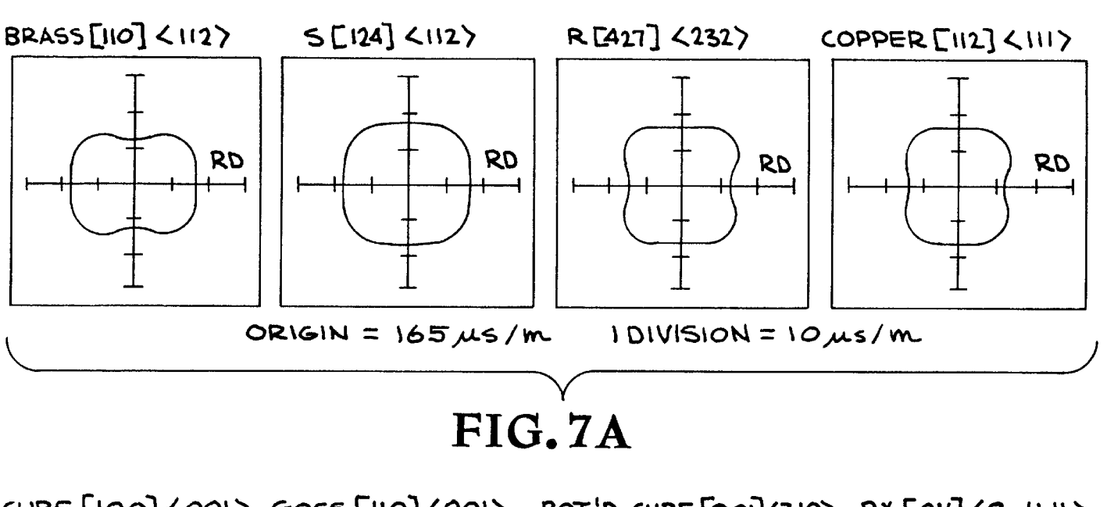
Figure 7B:
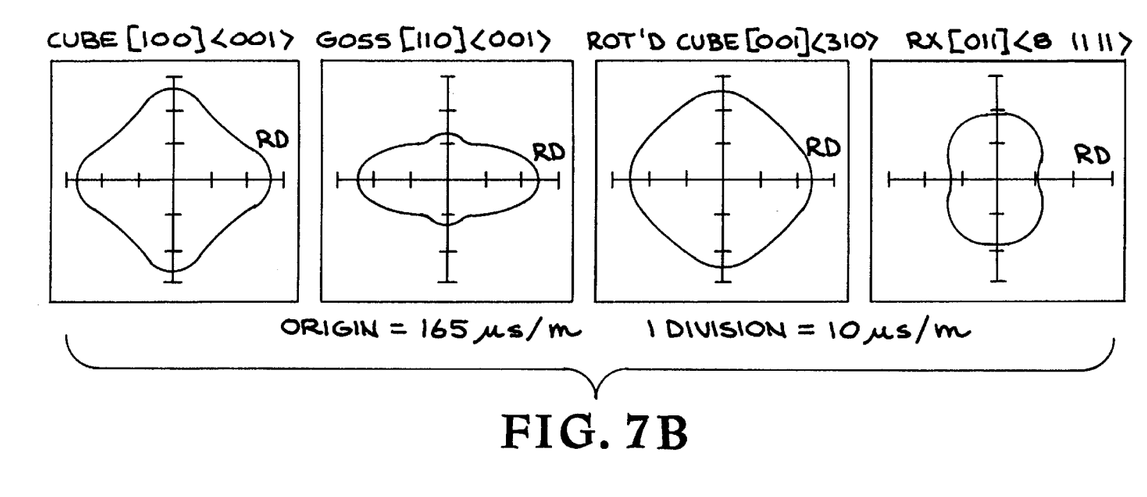
Figure 8A:
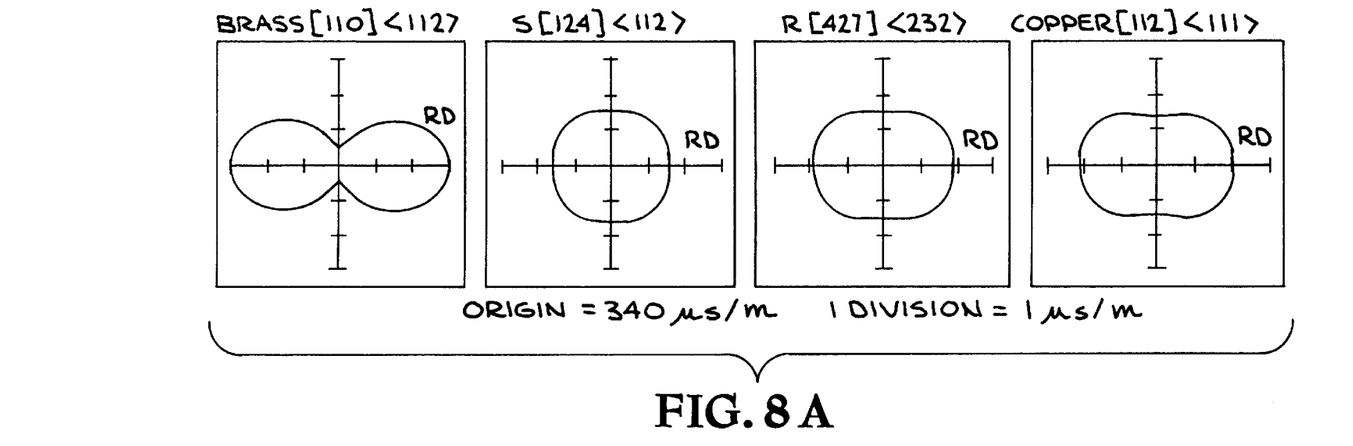
Figure 8B:
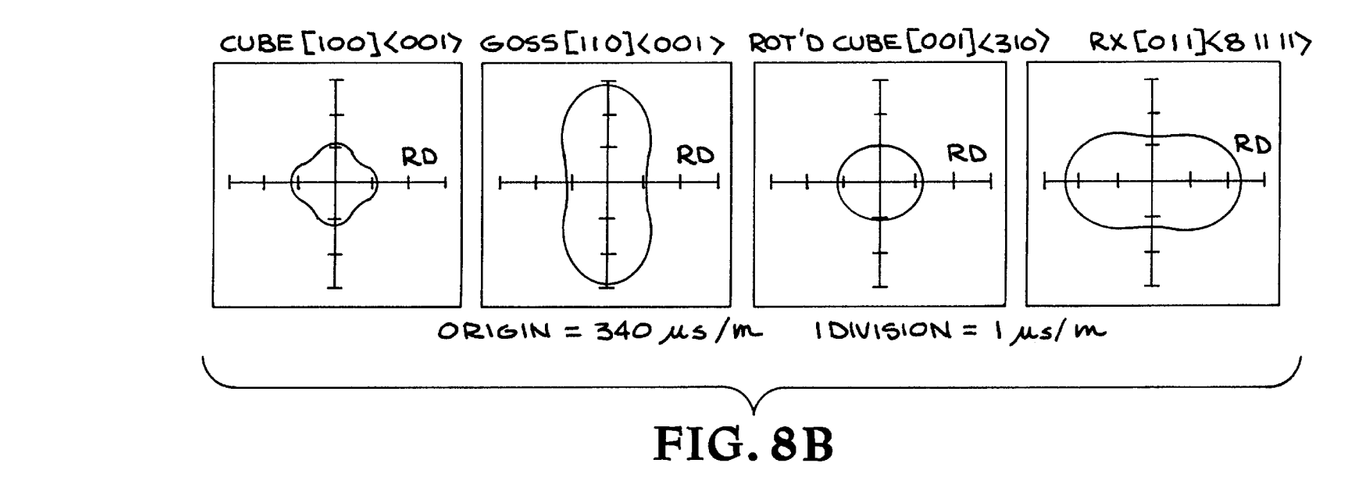

The coefficients $\alpha_i$ which describe this fitted curve are decomposed using, as a basis set, slowness curves for various textures which are precalculated from theory for the particular wave type(s) and mode(s), see FIGS. 6–8. For purposes of analysis and comparison it is convenient to express the slowness curves as a polar plot as a function of angle relative to, for example, the rolling direction. Examples of these curves for an aluminum sample are shown in FIG. 4. The data points 410 are extracted from the time windows depicted in FIG. 3c as a function of angle relative to the rolling direction. The data points 410 are joined by a curve 420 generated from Equation (1) and fitted to the data points by means of the coefficients $\alpha_i$. Experimentally derived slowness curves are compared with those calculated from theory, as shown in FIGS. 6–8, in order to determine the major texture components.

Figure 5:
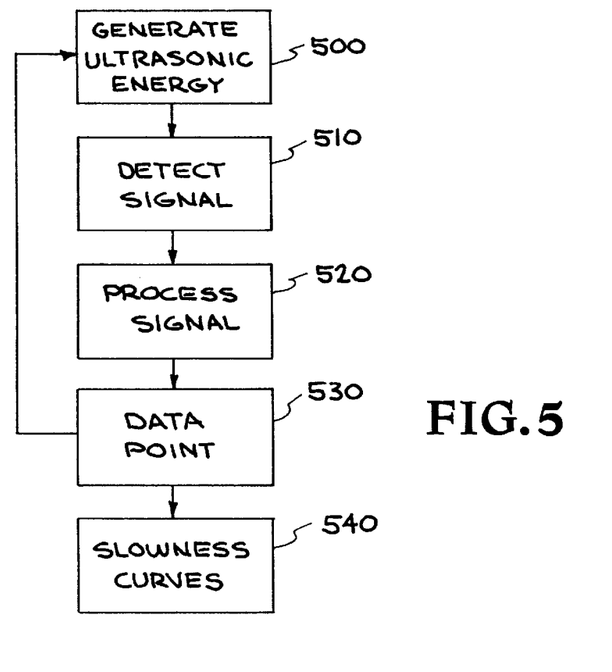
FIG. 5 shows a process flow for the method of the instant invention.

With the aid of FIG. 5 the process of the present invention will be described in more detail. FIG. 5 represents a processing flow diagram according to the present invention. Referring now to FIG. 5, as previously described and now shown in step 500, complex ultrasonic energy is generated in a sample. At step 510, a complex signal representative of the ultrasonic energy propagation in the sample is detected. At step 520, the signal is then processed with processor 170 of FIG. 1 to first determine a time window within the signal which represents the most likely time of arrival for a given mode or type of ultrasonic wave. That portion of the signal within the time window is then correlated with a reference waveform for a particular wave type or mode. The process of steps 500–530 is repeated for a plurality of orientations to produce polar diagrams depicted in FIG. 6–8. Repeating steps 500–530 for a plurality of orientations, the resulting slowness can be plotted using the curve fitting algorithm set forth in Eq. 1 above and polar diagrams similar to those depicted in FIGS. 6–8 can be generated in step 540.

We claim:

1. A method of determining a physical characteristic of a material, comprising the steps of:

a) generating a complex acoustic wave in a known material to be evaluated by a triggering a wave generating means, said wave generated at a known point on a surface of said material, said complex acoustic wave comprising a plurality of wave components, said wave components comprising surface waves and bulk waves, said surface and bulk waves having differing modes, said modes having differing velocities of propagation, said surface having a plane, said surface having further an axis in said plane;

b) starting a timing means which is automatically triggered upon triggering said wave generating means;

c) detecting said complex acoustic wave as a disturbance on said surface of said material to be evaluated by a detecting means, said disturbance generating a measurable signal, said signal comprising a complex sinusoidal wave having a plurality of maxima and minima, said detecting means and said wave generating means separated by a known separation distance;

d) processing said signal by setting a time gate and selecting only the largest maxima occurring within said time gate, said time gate comprising a first time and a later second time, said first and second times measured from said triggering of said timing means, said first and said second times chosen based upon said known separation distance and a known velocity of sound on said material surface;

e) determining a velocity of propagation of said surface waves in a plurality of differing directions relative to said point on said surface in order to obtain velocity data wherein an orientation is associated with a surface wave velocity;

f) normalizing said each of said surface wave velocities using one of said velocities measured along a preselected orientation relative to said axis of said surface;

g) fitting said velocities data and said associated orientations to a curve by a numerical means;

h) displaying said curve as a polar coordinate representation of said velocity data and said associated orientations; and i) inferring a physical characteristic of said material to be evaluated from said representation.

2. The method of claim 1 wherein the wave generating means comprises illuminating the material to be evaluated with a pulse laser, said laser having pulses with sufficient energy and limited duration for rapidly and briefly heating a localized spot on said surface of said material.

3. The method of claim 1 wherein the physical characteristic is selected from the group consisting of density, texture, stress, strain, tensile strength, elastic constants, grain size and orientation, ductility and combinations thereof.

4. The method of claim 1, wherein the wave generating means comprises the use of a source which does not physically contact the material.

5. The method of claim 1, wherein said detector means which does not physically contact the material to be evaluated.

6. The method of claim 1 wherein said numerical means further comprises constructing a diagrammatic representation displaying said velocity of propagation as a function of the orientation associated with each of said velocities.

7. The method of claim 1, wherein the material is selected from a group consisting of metals, polymers and glasses.

8. The method of claim 1 wherein the material is compacted powders.

* * * * *